United States Patent [19]

Hawman

[11] Patent Number: 4,752,691

[45] Date of Patent: Jun. 21, 1988

[54] METHOD AND APPARATUS FOR COMPENSATING FINITE ANGULAR RESOLUTION IN COLLIMATED SCINTILLATION CAMERAS

[75] Inventor: Eric G. Hawman, Buffalo Grove, Ill.

[73] Assignee: Siemens Gammasonics, Inc., Des Plaines, Ill.

[21] Appl. No.: 877,617

[22] Filed: Jun. 23, 1986

[51] Int. Cl.$^4$ .................. G01T 1/161; G01T 1/166
[52] U.S. Cl. .................. 250/363 S; 378/10; 378/19
[58] Field of Search ............... 250/363 SH, 363 SF, 250/363 SC, 363 SB, 363 SR; 378/19, 10

[56] References Cited

U.S. PATENT DOCUMENTS 4,262,207 4/1981 Tosswill .................. 250/363 S

OTHER PUBLICATIONS

M. A. King et al., "Two-Dimensional Filtering of SPECT Images Using the Metz and Wiener Filters", *Journal of Nuclear Medicine*, vol. 25, pp. 1234-1240 (1984).
B. R. Frieden, "Image Restoration by Discrete Convolution of Minimal Length", *Journal of the Optical Society of America*, vol. 64, pp. 682-686 (1974).
B. E. A. Saleh, "Trade Off Between Resolution and Noise in Restoration by Superposition of Images", *Applied Optics*, vol. 13, No. 8, pp. 1833-1838.
R. S. Hsieh et al., "On Methods of Three-Dimensional Reconstruction From a Set of Radioisotope Scintigrams", *IEEE Transactions of Systems, Man, and Cybernetics*, vol. SMC-6, No. 12, pp. 854-862 (Dec. 1976).
O. Ying-Lie, "An ECAT Reconstruction Method Which Corrects for Attenuation and Detector Response", *IEEE Transactions on Nuclear Science*, vol. NS-30, No. 1, pp. 632-635 (Feb. 1983).

*Primary Examiner*—Janice A. Howell
*Assistant Examiner*—Constantine Hannaher
*Attorney, Agent, or Firm*—Mark H. Jay

[57] ABSTRACT

Image data are acquired of an object along a given nominal view direction as well as at other view directions which are slightly off-axis with respect to the nominal view direction. The image data is used to produce an enhanced image of the view along the nominal view direction and to compensate for at least some of the effects of finite angular resolution of the camera collimator.

6 Claims, 9 Drawing Sheets

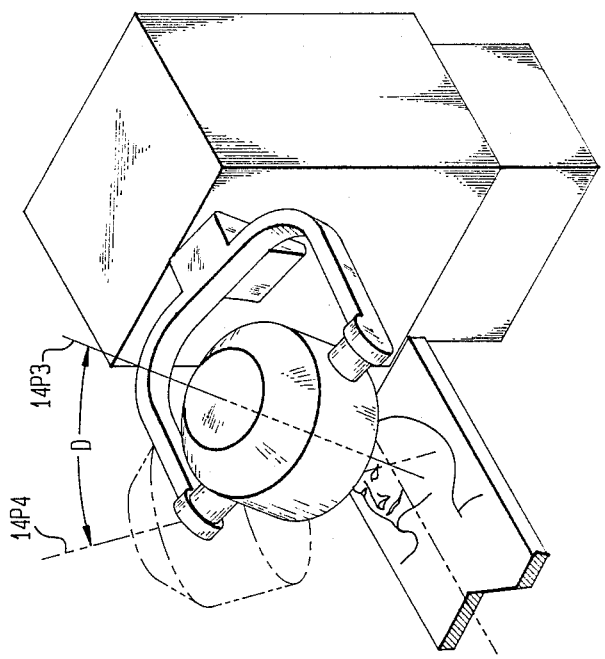
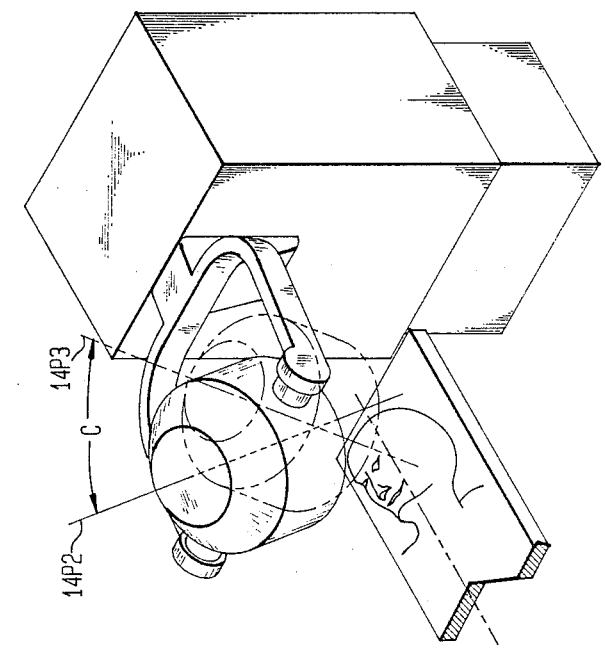

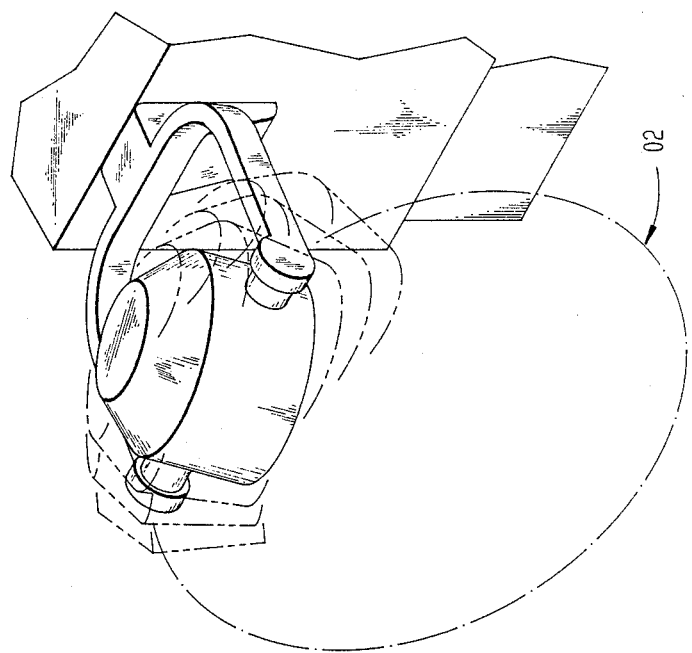
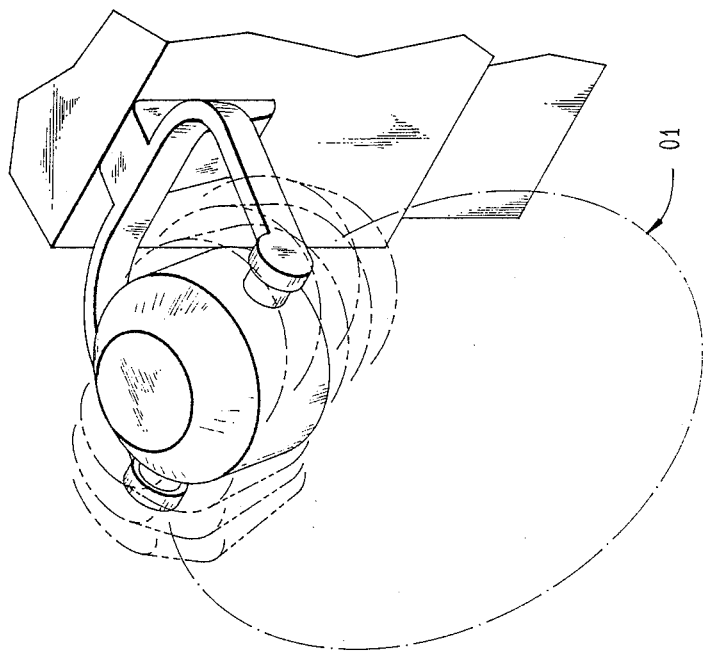

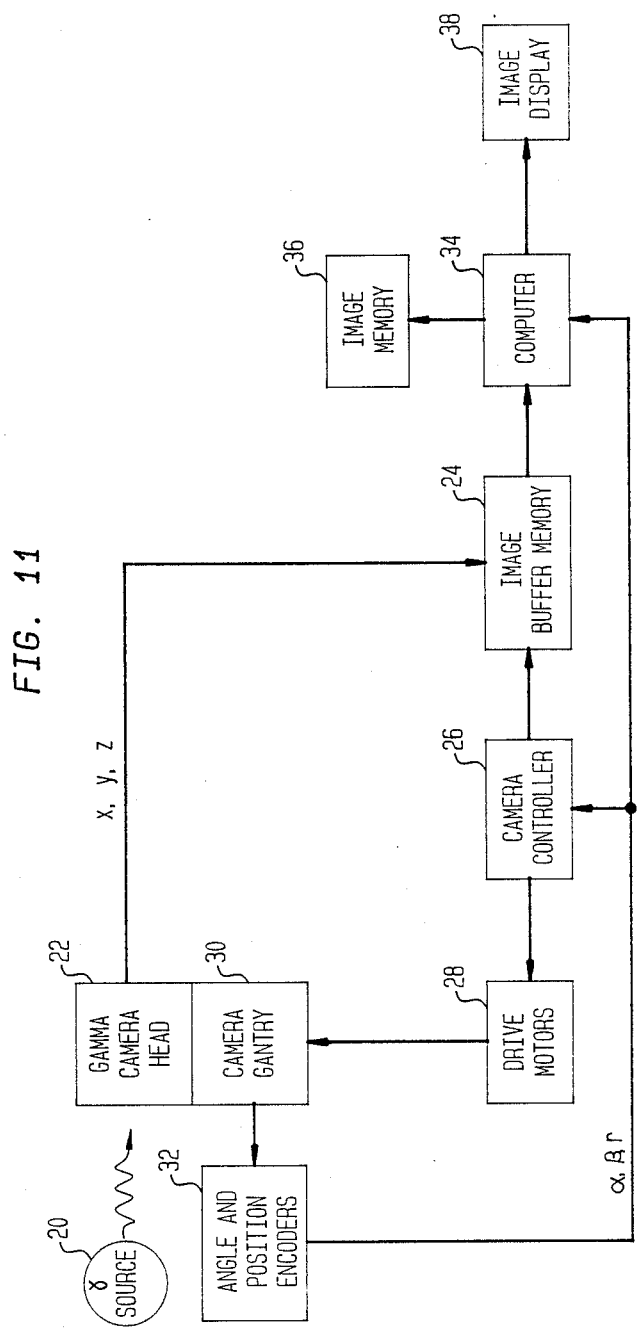

METHOD AND APPARATUS FOR COMPENSATING FINITE ANGULAR RESOLUTION IN COLLIMATED SCINTILLATION CAMERAS

BACKGROUND OF THE INVENTION

The invention relates to scintillation cameras, and more particularly relates to compensating for the effect of finite angular resolution of collimated scintillation cameras.

In a conventional scintillation camera as used for example in medicine, a collimator is mounted to the face of the camera. The collimator collimates the radiation which has passed through the patient before that radiation strikes the sensitive crystal surface of the camera.

Each channel of an ideal collimator would be infinitely narrow. If this were possible, each channel of the collimator would permit only on-axis rays to reach the sensitive surface; all other rays, no matter how slightly off-axis, would be blocked. Put another way, the scintillation camera system would have an infinitesimal angular resolution because no off-axis ray would ever be able to get through the collimator.

An ideal collimator cannot be manufactured. Each collimator channel must be finitely wide and deep. Hence, off-axis rays can and do reach the sensitive crystal surface, so that the angular resolution of the camera is finite.

Because of this, there is an inherent limitation on the resolving ability of the camera. As a result, highly detailed regions of the image cannot be accurately depicted because the detail is finer than the camera's limit of angular resolution.

The finite angular resolution of the system becomes increasingly important with increasing distance between the patient and the sensitive crystal surface. This is because the region subtended by the minimum resolvable angle becomes larger with increasing distance from the collimator. Therefore, the detail in the final image of the patient depends upon the distance between the imaged region and the camera head. To maximize this detail, a technician must spend the time to minimize the distance between the camera head and the patient over the whole range of motion of the camera head. This decreases patient throughput through the scintillation camera.

It is known to apply correction techniques to compensate scintillation camera systems for various factors, but the factors do not include compensation for finite angular resolution. For example, there exist conventional techniques by which the camera is corrected for spatial nonlinearity and nonuniform energy response; in these correction schemes, a fixed camera is exposed to e.g. a test pattern and/or a full-field flood in order to derive correction factors to be applied to incoming image data on an event-by-event basis. These latter techniques correct neither for finite angular resolution nor for any collimator-related factor.

One object of the invention is to provide a scintillation camera system which corrects for the finite angular resolution of its collimator.

Another object is to provide such a system in which distance between the patient and the camera is less critical a factor than it is now.

Yet another object is to provide such a system which permits the in situ compensation of individual collimators.

Still another object is to provide such a system which has a better angular resolution than its constituent collimator.

Still a further object is to provide such a system in which it is possible to improve the angular resolution without changing the collimator.

Yet a further object is, in general, to improve on known devices of this type.

SUMMARY OF THE INVENTION

In accordance with the invention, the nonzero angular resolution of a collimator is compensated. This is done by mounting the collimator to the camera and then using the collimated camera system to acquire an additional set of views which are then used in a non-conventional manner.

More specifically, for each view of an object taken along a nominal view direction, there are acquired a plurality of additional views, each displaced by a small angle from the nominal view direction. The additional views acquired are then used to produce an enhanced image along the nominal direction of view, and only enhanced image data is used to form the final planar or tomographic image.

Advantageously, the additional views are acquired by:
(a) rocking the camera through a relatively small angle in at least two directions; or
(b) adding additional orbits to a conventional SPECT view acquisition scheme.

In one preferred embodiment the camera is nutated (i.e. rotated by a small angle) in four directions (advantageously by one-half of the beam width of the collimator) with respect to the nominal direction of view. In another preferred embodiment, a rotating camera head is nutated by one-half of the beam width of the collimator and executes two additional orbits at the negative and positive nutated angles.

The invention is to be distinguished from the conventional tomographic image acquisition techniques used in scintillation camera processes. In these, the camera acquires views of the object from different directions in order to backproject the image data in the views to form a three-dimensional image. In accordance with the invention, additional views are used to enhance the image data in the conventionally acquired views of the object, and the enhanced image data, rather than the unenhanced image data, are used to compose the final image.

BRIEF DESCRIPTION OF THE DRAWINGS

Exemplary and non-limiting preferred embodiments of the invention are shown in the drawings, in which:

FIGS. 8A-8E show the operation of a preferred embodiment of the invention set up for the same study as is performed in FIG. 7;

FIGS. 10A and 10B illustrate a preferred embodiment of the invention set up for forming a tomographic image;

FIG. 11 is a block diagram of a preferred embodiment of the invention;

DETAILED DESCRIPTION OF PREFERRED EMBODIMENTS

Figure 1:
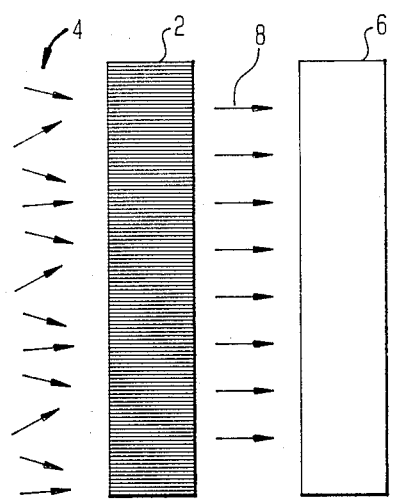
FIG. 1 is a schematic illustration of a collimated scintillation camera head.
Figure 2:
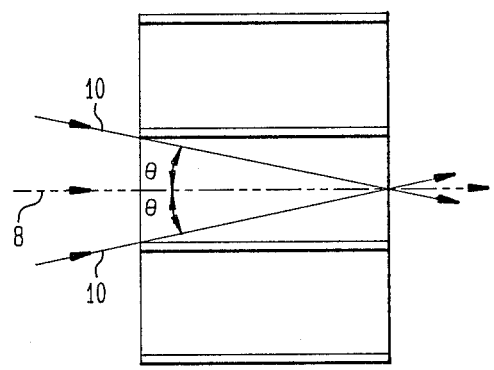
FIG. 2 illustrates how an image is blurred by finite angular resolution of a collimator.

As is shown in FIG. 1, a collimator 2 is used to collimate radiation generally indicated by refernce numeral 4 before the radiation 4 reaches a scintillation camera head 6. An ideal collimator 2 would block all off-axis rays, so that only on-axis radiation 8 would reach the sensitive crystal surface. (It will be understood that although a parallel-hole, nonfocusing collimator is illustrated, this is only for convenience and the invention applies equally well with astigmatic collimators and focusing collimators such as fan-beam collimators and cone-beam collimators). As is shown in FIG. 2, the collimator 2 has a finite angular resolution, i.e. does not permit only on-axis rays 8 from reaching the head 6. Rather, rays 10 which are off-axis by an angle $\theta$ (which may be as much as 5 degrees) will pass through the collimator 2. While this non-zero angle $\theta$ can be cut down by making the channels of the collimator 2 smaller, a non-zero angular resolution is inherent in all collimators because it is impossible to manufacture a collimator with infinitesimally thin channels. (FIGS. 1 and 2 are not to scale and have been enlarged for clarity).

Figure 3:
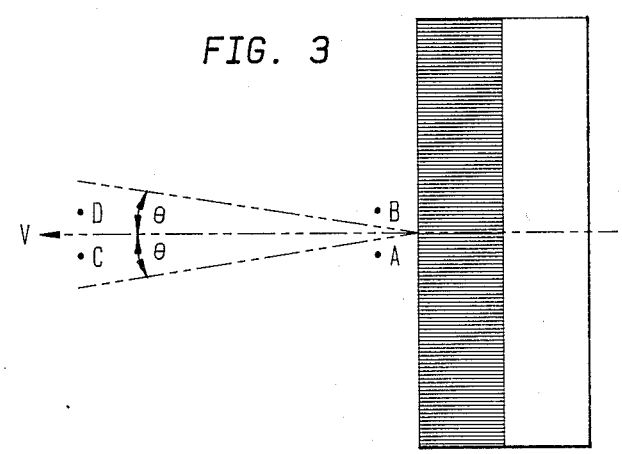
FIG. 3 illustrates how the spatial resolution of the final image depends upon the distance from the camera head.

Therefore, there is always a limit to the spatial resolution of the image produced by a conventional scintillation camera system, because the angular resolution of the collimator places a limit on the whole system. This limit is not only a function of the angular resolution of the collimator 2, but also depends upon distance from the collimator 2. As is illustrated in FIG. 3, the scintillation camera is able to distinguish between points A and B, but not between points C and D. This is because points C and D are far enough away from the collimator 2 so that they are both included in the cone of ambiguity defined by the finite angle of resolution about the nominal direction of view V. (FIG. 3 is not to scale and has been exaggerated for clarity).

Figure 4:
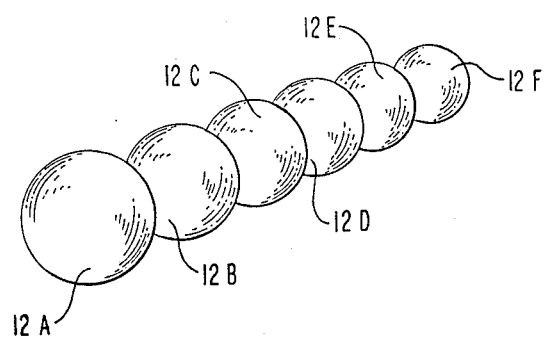
FIG. 4 illustrates how an ideally collimated camera system would image a phantom.
Figure 5:
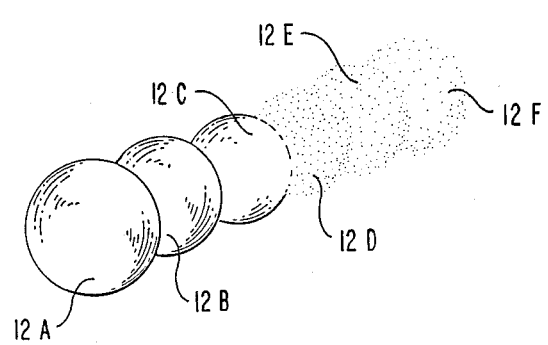
FIGS. 5 and 6 illustrate the effects of finite angular resolution of the final image of the FIG. 4 phantom.
Figure 6:
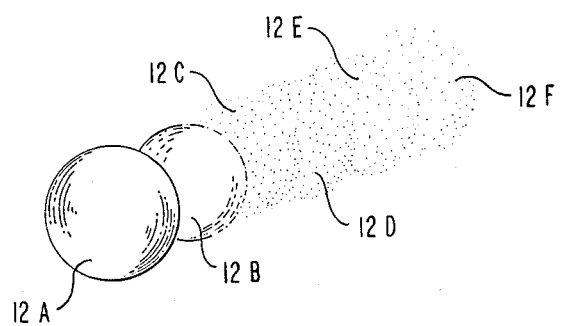

The consequences of improvements in the angular resolution of a scintillation camera system will now be illustrated with reference to FIGS. 4, 5 and 6. FIG. 4 shows an ideally collimated tomographic image of a test phantom, i.e. an image formed using an idealized collimator with an infinitesimal angular resolution. The phantom contains a row of spheres 12A-12F, with sphere 12A being nearest to the collimator and sphere 12F being furthest away. As is illustrated, all of the spheres 12A-12F are equally sharply focused, even though they are at different differences from the collimator.

However, where the collimator is non-ideal and has a finite (as opposed to an infinitesimal) angular resolution, the image is blurred, the degree of blurriness increasing with increasing distance from the collimator. Thus, while the nearest spheres (sphere 12A' in FIG. 5 and sphere 12A" in FIG. 6) are still in focus, the spheres become progressively less focused, with the last spheres 12F' and 12F" being extremely blurry. The rate at which the blurriness of the image increases with increasing distance is dependent upon the angular resolution of the collimator, which can be seen by a comparison of FIG. 5 with FIG. 6.

In accordance with the invention, the angular resolution of the system is improved not by making physical improvements to the collimator but rather by enhancing the image data acquired of the object under investigation.

This in turn is accomplished by correcting the image data in each view which is to be used in the composition of the final image, using image data taken from closely spaced but nonetheless different adjacent views. In one preferred embodiment, the camera head is brought to a position in which an image is formed along a nominal direction of view and the camera head is then nutated in four directions through an angle of half the beam width. This is preferable when forming planar images of an object under investigation.

Alternatively, where tomographic images are formed from a large number of views acquired during a 360° orbit of the camera head about an axis, the adjacent views are acquired in other orbits of the camera head about the patient. In this alternative, individual views may be used for two purposes. In the first, the image data in the view is corrected using information from other closely adjacent views and then used (as by back-projection or otherwise) to form a final tomographic image. In the second, the image data in the view is used to correct the image data in a closely adjacent view without itself being included as such in the final image.

The word "nutation", as used herein, encompasses the concept of a relatively small angular motion between two endpoints, without reference to the path traversed by the camera head between those two endpoints. The exact path traversed by the camera head is not a part of this invention.

In the following discussion, the application of the invention to planar imaging will be discussed first. The application of the invention to tomographic imaging will be discussed next.

Figure 7:
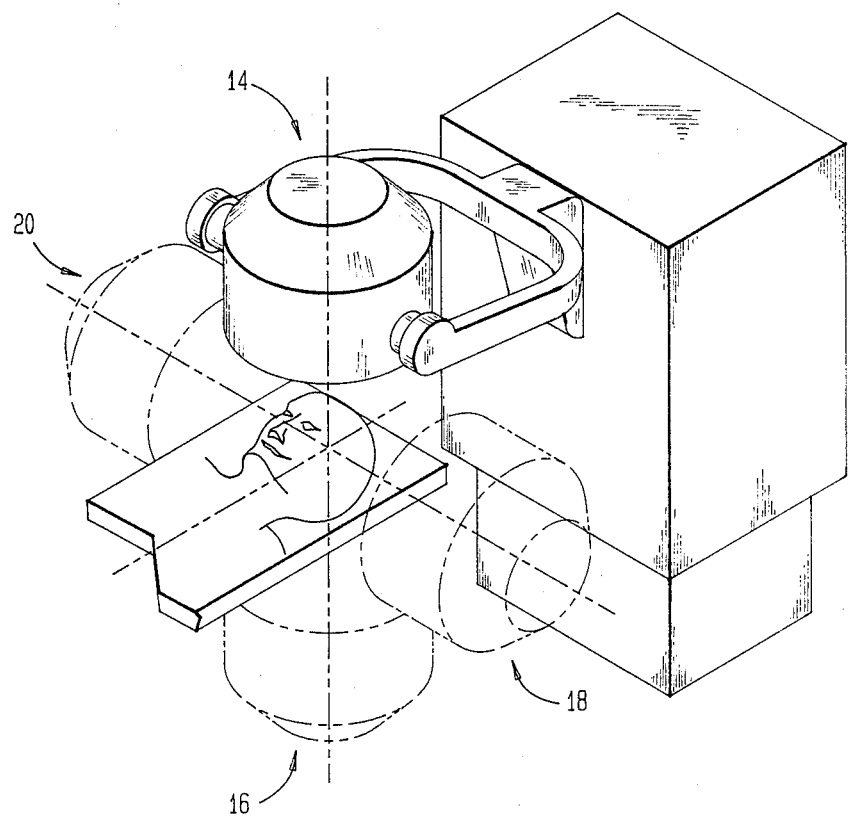
FIG. 7 shows a scintillation camera system set up for conducting a four-view planar study of a patient's brain.
Figure 8B:
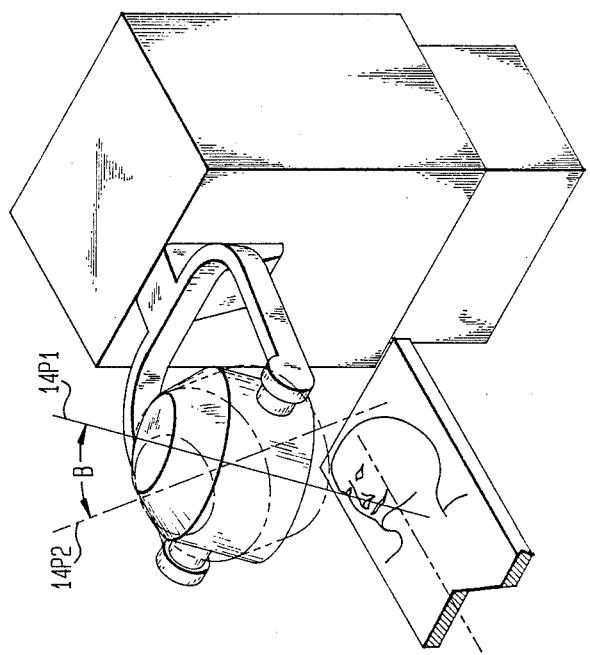
Figure 8A:
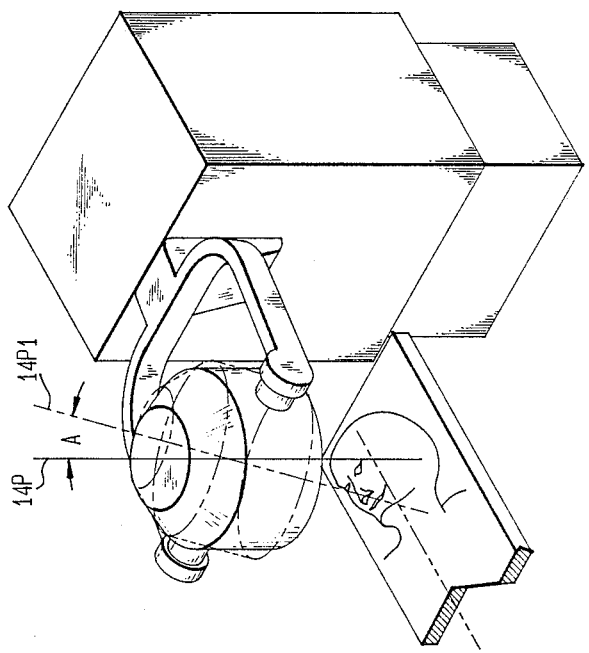
Figure 8E:
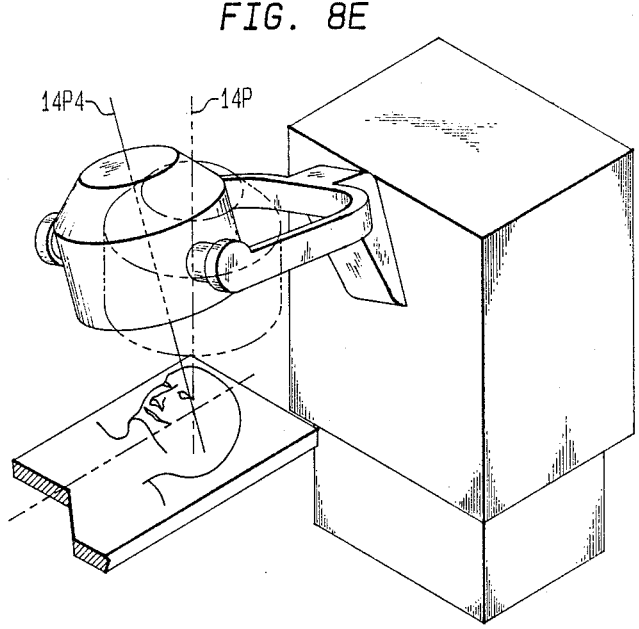

In a conventional brain study, illustrated in FIG. 7, four views are taken: an anterior view 14, a posterior view 16, a left lateral view 18, and a right lateral view 20. In accordance with the invention as illustrated in FIGS. 8A-8E, the scintillation camera head with the collimator attached is rotated to, e.g., a position 14P in which it has an anterior view of the patient's brain, and one view is acquired. The scintillation camera head is then nutated by half the beam width of the collimator to four closely adjacent positions 14P1, 14P2, 14P3 and 14P4 as shown in FIGS. 8A-8E and an additional view is acquired at each position. In these Figures (which are not to scale and which has been exaggerated for clarity), the initial position of the camera head is indicated in solid lines; the next position of the camera head is indicated in dotted lines. In this example, the directions of nutation are chosen to coincide with the standard motions that can be executed by the camera head; nutations A and B are carried out by rotating the camera head within the yoke and nutations C and D are carried out by rotating the yoke itself. However, this is done only for convenience and other directions of nutation could alternatively be chosen. The mechanisms by which the nutations are carried out are not shown specifically because such mechanisms are known by themselves and are conventionally included in modern, motor-driven camera systems.

The views at the adjacent positions 14P1 through 14P4 are then used to correct the anterior view 14P to form an enhanced anterior view of the patient's brain. A similar procedure is carried out at each of the other three positions 16, 18 and 20. The result is four planar views of the patient's brain, each view having an improved spatial resolution.

Figure 9:
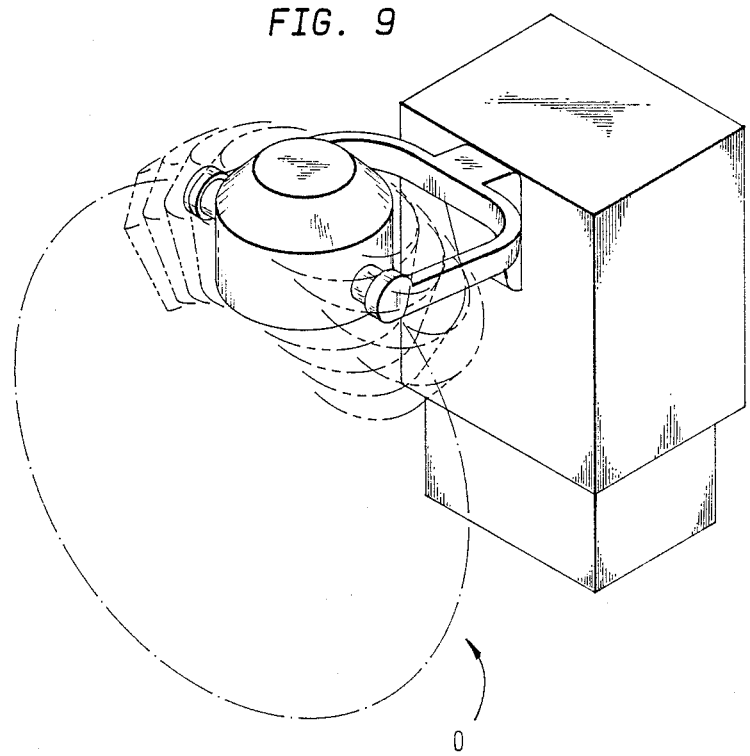
FIG. 9 shows one orbit of the scintillation camera system set up for forming a tomographic image.

For computerized tomography, the operation according to FIGS. 8A-8E would be unfeasible. The time required to (a) move the camera head to each of the locations from which a view is taken to form a tomographic image and then to (b) nutate it at each location before going on the next location would be excessive, because a tomographic image is commonly made up of between 64 and 128 views. Accordingly, the camera head with collimator attached is caused to execute, e.g. three orbits about the patient. In one orbit O (FIG. 9), views along the nominal directions of view are acquired as in conventional SPECT. In the other two orbits O1 and O2 (FIGS. 10A and 10B), the camera head is nutated by half the beam width of the collimator and remains at its new angle for the duration of the orbit. Consequently, to speed the data acquisition process, the various views of the object to be imaged are all acquired first and the data in those views are enhanced and backprojected only later. (FIGS. 9, 10A and 10B are not to scale and have been exaggerated for clarity.)

It will be understood by those skilled in the art that the number and duration of the nutated views can be selected to optimize whatever factors are considered important. Therefore, the orbits of the camera in its nutated positions may be more rapid than the main orbit. In high activity or longer time studies it may be useful to acquire more than two nutated views. However, where an isotope of lesser activity is used, the additional information contributed by more nutated views may be insufficient, because of signal-to-noise considerations, to justify this.

The method by which the enhancement of the views along the nominal view directions and the correction of the image data is carried out will now be discussed.

In accordance with the invention, radiation from a gamma radiation source 20 is incident upon a collimated scintillation camera head 22. The head 22 produces electrical signals representing the location and energy of detected scintillation events. This information is routed to an image buffer memory 24.

A camera controller 26 controls the buffer memory 24 and also controls appropriate drive motors 28 which are used to adjust the pitch, yaw and radius of the head 22. The drive motors 28 move the camera gantry 30 to which the head 22 is attached. Angle and position encoders 32 are connected to the gantry 30 and produce electrical signals representing the current position of the head 22. These signals are routed to the controller 26 and to an image processing computer 34. The image processing computer 34 takes the image data contained in the buffer memory 24 and processes it to construct an image in image memory 36. After the image has been calculated, it can then be displayed on image display 38.

The controller 26 is programmed so that when a particular study is selected, the appropriate positions or orbits of the head 22 are correspondingly chosen. The head 22 is then moved appropriately for the study selected, and the image data acquired processed in the computer 34 without the necessity of manual adjustment of the head 22 after the study has begun.

The method by which the compensation for finite angular resolution is accomplished will now be described, first for the case of tomographic imaging, and next for the case of planar imaging.

TOMOGRAPHIC IMAGING

Figure 12:
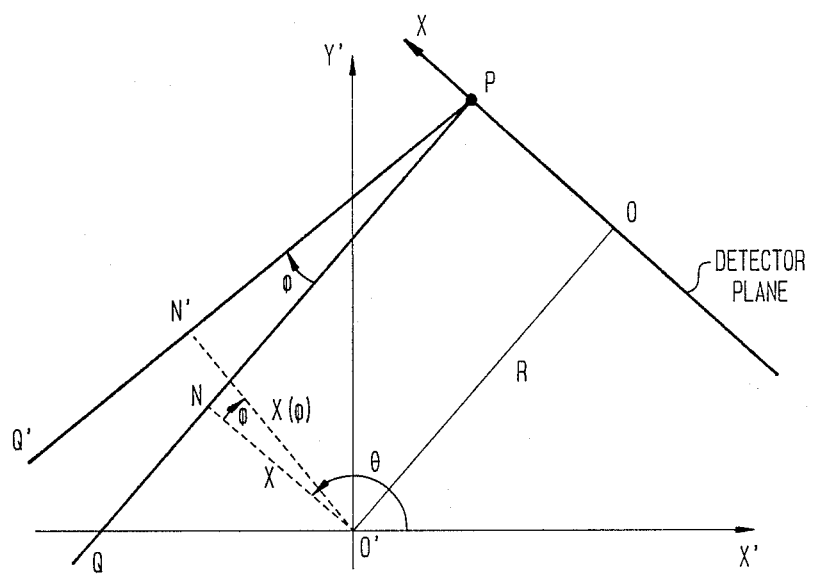
FIG. 12 is a diagram illustrating the geometry involved in producing an enhanced tomographic image.

The case of tomographic imaging will be discussed with reference to FIG. 12. Any point P on the plane of the detector may receive radiation from a certain angular range, the finite angular resolution of the collimator. This angular beam may be characterized by a certain distribution function, $w(\Phi)$. Using this function, the projection with finite angular beam width can be related to the set of projections with infinitesimal beam width, $p(x,\theta)$ (the ideal projection set). Let $q(x,\theta)$ be the finite angular resolution projection at angle $\theta$. The intensity at P is a weighted summation of radiant flux from different angles. Each ray is characterized by two coordinates, the normal from the origin, $x(\Phi)$, and the polar angle, $\theta-\Phi$. The relation of $q(x,\theta)$ and $p(x,\theta)$ is $$q(x,\theta) = \int_{-\infty}^{\infty} w(\phi)p[x(\phi), \theta - \phi]d\phi \quad (1)$$

This relation is similar to a convolution, but differs in the dependence of the projection on $x(\Phi)$. Let x be the normal distance NO' for the ray QP, which is normal to the detector plane, see FIG. 12. The distance $x(\Phi)$ is given by $$x(\Phi) = x \cos \Phi + R \sin \Phi \quad (2a)$$

Conventional collimators define a narrow (5° and less) beam, so the small angle approximations can be used. Hence, $$x(\Phi) = x + R\Phi \quad (2b)$$

and $$q(x,\theta) = \int_{-\infty}^{\infty} w(\phi)p[x + R\phi, \theta - \phi]d\phi \quad (3)$$

This expression can be regarded as specific two-dimensional linear filtering or convolution applied to the sinogram of the ideal projections $p(x,\theta)$. To see this, Fourier transforms can be taken with respect to spatial and angular coordinates.

Notation for the Fourier transforms is as follows:

$$Q(x,\bar{\theta}) = \int_{-\infty}^{\infty} q(x,\bar{\theta})^{-j2\pi\theta\bar{\theta}}d\theta \quad (4a)$$

and $$(x,\theta) = \int_{-\infty}^{\infty} Q(x,\bar{\theta})^{-j2\pi x\bar{x}}dx \quad (4b)$$

Transforms for $p(x,\theta)$ are defined similarly.

The Fourier transform of $w(\Phi)$ is:

$$(\phi) = \int_{-\infty}^{\infty} w(\phi)e^{-j2\pi\phi\phi}d\phi \tag{5}$$

Taking the complete Fourier transform on Equation (3) yields:

$$(x,\theta) = (x,\theta)(\theta - xR) \tag{6}$$

Thus the 2-D Fourier transforms of the finite angular resolution data can be obtained from the infinitesimal beam data by a two-dimensional filtering of the data.

Also, from Equation (6), it would be expected that an estimate of the pencil beam projection could be obtained by inverse filtering:

$$(x,\theta) = \frac{(x,\theta)}{(\theta - xR)} \tag{7}$$

However, an inverse filter estimate would be unstable or extremely noisy, because will be very small in magnitude outside of some domain. The estimate could be stabilized (regularized) using any of a number of techniques, for example, a form similar to Wiener filtering could be used:

$$(x,\theta) = \frac{(x,\theta) \cdot {}^*(\theta - xR)}{|(\theta - xR)|^2 + A} \tag{8}$$

where A is a constant which may be chosen to prevent excessive noise amplification, or to limit the maximum filter amplitude.

PLANAR IMAGING

Figure 13:
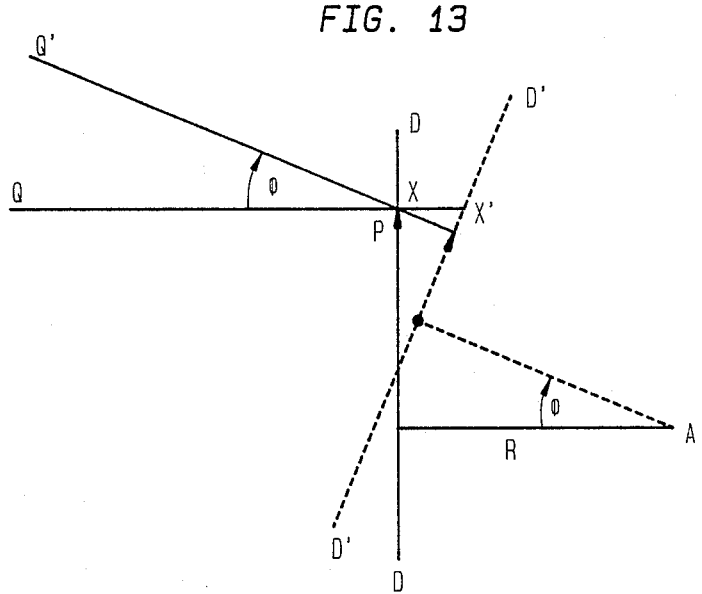
FIG. 13 is a diagram illustrating the geometry involved in producing an enhanced planar image.

In applying the invention to planar imaging, a number of image views are obtained by nutating the camera by small angles about the nominal view direction. FIG. 13 indicates two different detector positions, DD and D'D', which is rotated by $\Phi$ about a pivot A. Consider two rays, QP and Q'P, which correspond to detector coordinates x and x'. These coordinates are related by $x' = x\cos\Phi - R\sin\Phi$, or for small angles, $x' = x - R\Phi$.

A number of projection images with finite angular resolution, characterized by the collimator beam function $w(\theta)$, are acquired. The object of the invention is to utilize these multiple views to form a projection of enhanced angular resolution for the nominal beam direction.

One realization for the enhanced projection estimate would be a linear form as follows:

$$p(x) = \sum_k a_k q(x - kR\Delta\phi, k\Delta\phi) \tag{9}$$

where $q(x,k\Delta\Phi)$ = finite beam projection for an angle $k\Delta\Phi$, with respect to nominal view direction and $a_k$ = coefficients of linear estimator.

Using the relation between the finite and infinitesimal projections given by Equation (1), the projection estimate can be expressed as $$p(x) = \sum_k a_k \int_{-\pi/2}^{\pi/2} w(\phi)p[x + R(\phi - k\Delta\phi), k\Delta\phi - \phi]d\phi \tag{10}$$

Changing the variable of integration to $\Phi' = \Phi - k\Delta\Phi$, yields $$p(x) = \sum_k a_k \int_{-\pi/2}^{\pi/2} w(\phi' + k\Delta\phi)p[x + R\phi', -\phi']d\phi' \tag{11}$$

From this equation, a beam function characterizing the enhanced projection set can be identified.

$$p(x) = \int_{-\pi/2}^{\pi/2} h(\phi)p[x + R\phi, -\phi]d\phi \tag{12}$$

where the net beam function for the estimate is $$h(\phi) = \sum_k a_k w(\phi + k\Delta\phi) \tag{13}$$

The selection of coefficient $a_k$ to create or approximate a specific beam function is quite analogous to a filter design problem. The $a_k$ must be selected with regard to system resolution, sidelobe behavior, and noise propagation into the enhanced projection.

Those skilled in the art will understand that changes can be made in the preferred embodiments here described, and that these embodiments can be used for other purposes. Such changes and uses are within the scope of the invention, which is limited only by the claims which follow.

What is claimed is:

1. A method for correcting a scintillation camera system for finite angular resolution of a collimator used therewith, comprising the following steps:
   (a) nutating the camera's field of view of an object in at least two directions by a relatively small angle with respect to a nominal view direction;
   (b) acquiring image data at the nutated fields of view; and
   (c) using said image data to produce an enhanced image along said nominal view direction.

2. The method of claim 1, wherein said nutating step comprises the step of rotating the camera head.

3. The method of claim 1, further comprising the step of acquiring image data along the nominal view direction.

4. Apparatus for correcting a scintillation camera system for finite angular resolution of a collimator used on a scintillation camera head, comprising:
   (a) means for nutating the field of view of the collimated camera system by a relatively small angle with respect to a nominal direction of view; and
   (b) means for using image data acquired during such nutation to at least partially compensate for the finite angular resolution of the collimator and so as to produce an enhanced image along said nominal direction of views.

5. The apparatus of claim 4, further comprising means for tilting the camera head in two orthogonal directions.

6. The apparatus of claim 4, further comprising means for forming a tomographic image from a plurality of enhanced images.

* * * * *